(12) United States Patent
Majercak et al.

(10) Patent No.: US 8,372,141 B2
(45) Date of Patent: Feb. 12, 2013

(54) TWISTED ANCHORING BARB FOR STENT OF ABDOMINAL AORTIC ANEURYSM (AAA) DEVICE

(75) Inventors: David C. Majercak, Stewartsville, NJ (US); Jin S. Park, Parsippany, NJ (US)

(73) Assignee: Cordis Corporation

( * ) Notice: Subject to any disclaimer, the term of this patent is extended or adjusted under 35 U.S.C. 154(b) by 0 days.

(21) Appl. No.: 12/859,382

(22) Filed: Aug. 19, 2010

(65) Prior Publication Data

US 2010/0312330 A1  Dec. 9, 2010

Related U.S. Application Data

(62) Division of application No. 11/488,198, filed on Jul. 18, 2006, now Pat. No. 8,298,281.

(51) Int. Cl.
 *A61F 2/06* (2006.01)
(52) U.S. Cl. ............................................. 623/1.36
(58) Field of Classification Search .................. 623/1.36
 See application file for complete search history.

(56) References Cited

U.S. PATENT DOCUMENTS

| | | | | |
|---|---|---|---|---|
| 5,720,776 A * | 2/1998 | Chuter et al. | ............... | 623/1.36 |
| 5,843,164 A * | 12/1998 | Frantzen et al. | ............. | 623/1.16 |
| 5,843,167 A | 12/1998 | Dwyer et al. | | |
| 5,976,178 A * | 11/1999 | Goldsteen et al. | ........... | 623/1.13 |
| 6,036,702 A * | 3/2000 | Bachinski et al. | ............ | 606/153 |
| 6,120,432 A * | 9/2000 | Sullivan et al. | ................ | 600/36 |
| 6,186,942 B1 * | 2/2001 | Sullivan et al. | ................ | 600/36 |
| 6,206,912 B1 * | 3/2001 | Goldsteen et al. | ........... | 623/1.23 |
| 6,302,905 B1 * | 10/2001 | Goldsteen et al. | ............ | 623/1.1 |
| 6,514,196 B1 * | 2/2003 | Sullivan et al. | ................ | 600/36 |
| 6,517,573 B1 * | 2/2003 | Pollock et al. | ............... | 623/1.15 |
| 6,695,878 B2 * | 2/2004 | McGuckin et al. | ........... | 623/1.19 |
| 6,702,829 B2 * | 3/2004 | Bachinski et al. | ............ | 606/153 |
| 6,736,133 B2 * | 5/2004 | Bachinski et al. | ............ | 126/521 |
| 6,814,748 B1 * | 11/2004 | Baker et al. | .................. | 623/1.14 |
| 7,094,248 B2 * | 8/2006 | Bachinski et al. | ............ | 606/153 |
| 7,147,662 B1 * | 12/2006 | Pollock et al. | ............... | 623/1.36 |
| 7,168,427 B2 * | 1/2007 | Bachinski et al. | ............ | 126/521 |
| 7,211,095 B2 * | 5/2007 | Bachinski et al. | ............ | 606/153 |
| 7,404,824 B1 * | 7/2008 | Webler et al. | ................ | 623/2.36 |
| 7,578,829 B2 * | 8/2009 | Goldsteen et al. | ............ | 606/153 |
| 7,850,705 B2 * | 12/2010 | Bachinski et al. | ............ | 606/153 |
| 2001/0010006 A1 * | 7/2001 | Bachinski et al. | ............ | 606/153 |
| 2001/0010007 A1 * | 7/2001 | Bachinski et al. | ............ | 606/153 |

(Continued)

FOREIGN PATENT DOCUMENTS

| | | |
|---|---|---|
| EP | 0712614 A1 | 5/1996 |
| JP | 8-299456 A | 11/1996 |
| WO | WO 02/100297 A | 12/2002 |
| WO | WO 2004/006983 A2 | 1/2004 |

OTHER PUBLICATIONS

European Search Report for Application EP 07 25 2732.8 dated Sep. 24, 2007.

(Continued)

*Primary Examiner* — William H. Matthews

(57) ABSTRACT

A stent is provided for an endoprosthesis having a main body portion and two leg portions, particularly suitable for treatment of an abdominal aortic aneurism. The stent includes barbs that are twisted and shaped set to point radially outward. Each barb, as formed, points substantially perpendicular relative to the longitudinal axis of the stent, even when in a non-deployed configuration. The motion to move the barb into a deployed configuration for gripping tissue is a twisting motion which moves the barb from being substantially aligned with the circumference of the stent to extending radially outwards from the stent.

7 Claims, 7 Drawing Sheets

U.S. PATENT DOCUMENTS

| | | | | |
|---|---|---|---|---|
| 2001/0041931 A1* | 11/2001 | Goldsteen et al. | | 623/1.23 |
| 2002/0022857 A1* | 2/2002 | Goldsteen et al. | | 606/185 |
| 2003/0220683 A1* | 11/2003 | Minasian et al. | | 623/1.15 |
| 2004/0117004 A1* | 6/2004 | Osborne et al. | | 623/1.36 |
| 2005/0096750 A1* | 5/2005 | Kagan et al. | | 623/23.65 |
| 2005/0240259 A1* | 10/2005 | Sisken et al. | | 623/1.36 |
| 2008/0033534 A1* | 2/2008 | Cook et al. | | 623/1.36 |
| 2009/0171442 A1* | 7/2009 | Young et al. | | 623/1.15 |

OTHER PUBLICATIONS

Office Action for Application EP 07252732.8 dated Nov. 11, 2008.
Japanese Notification of Reasons for Refusal mailed on Feb. 7, 2012 from corresponding Japanese Patent Application No. 2007-186016.

* cited by examiner

FIG. 3
FIG. 4
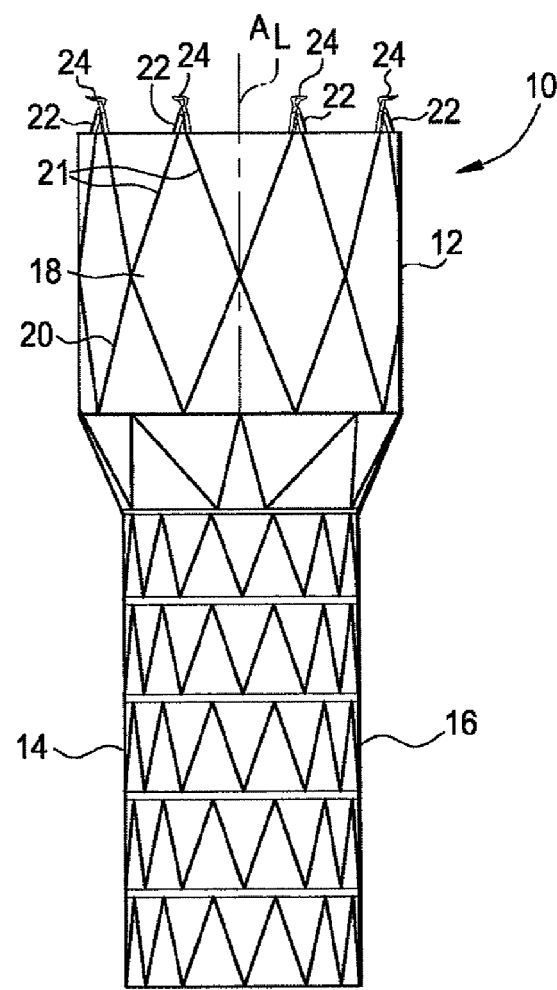
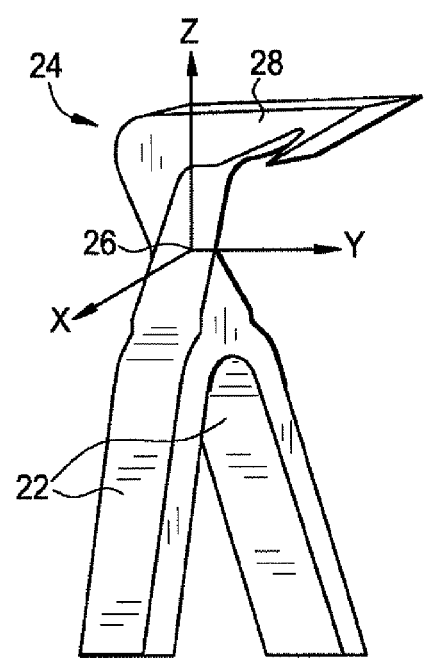

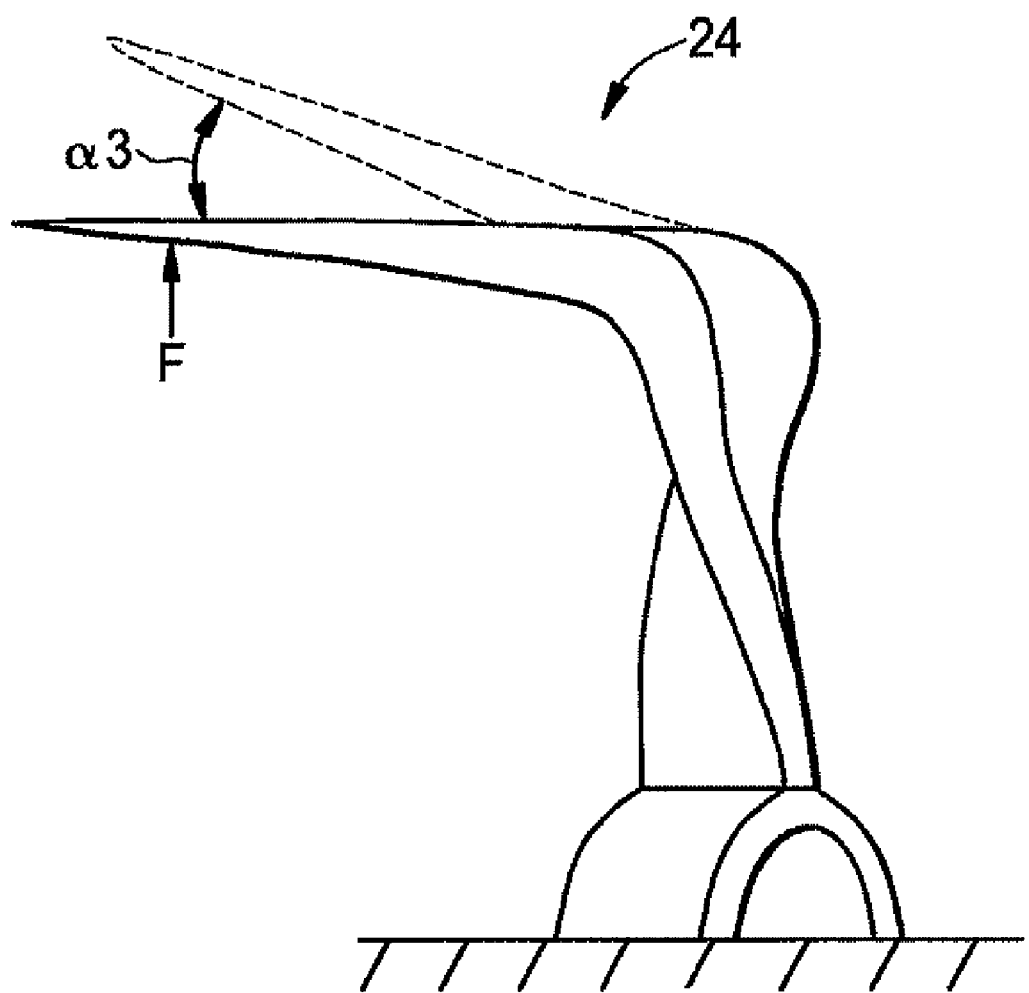

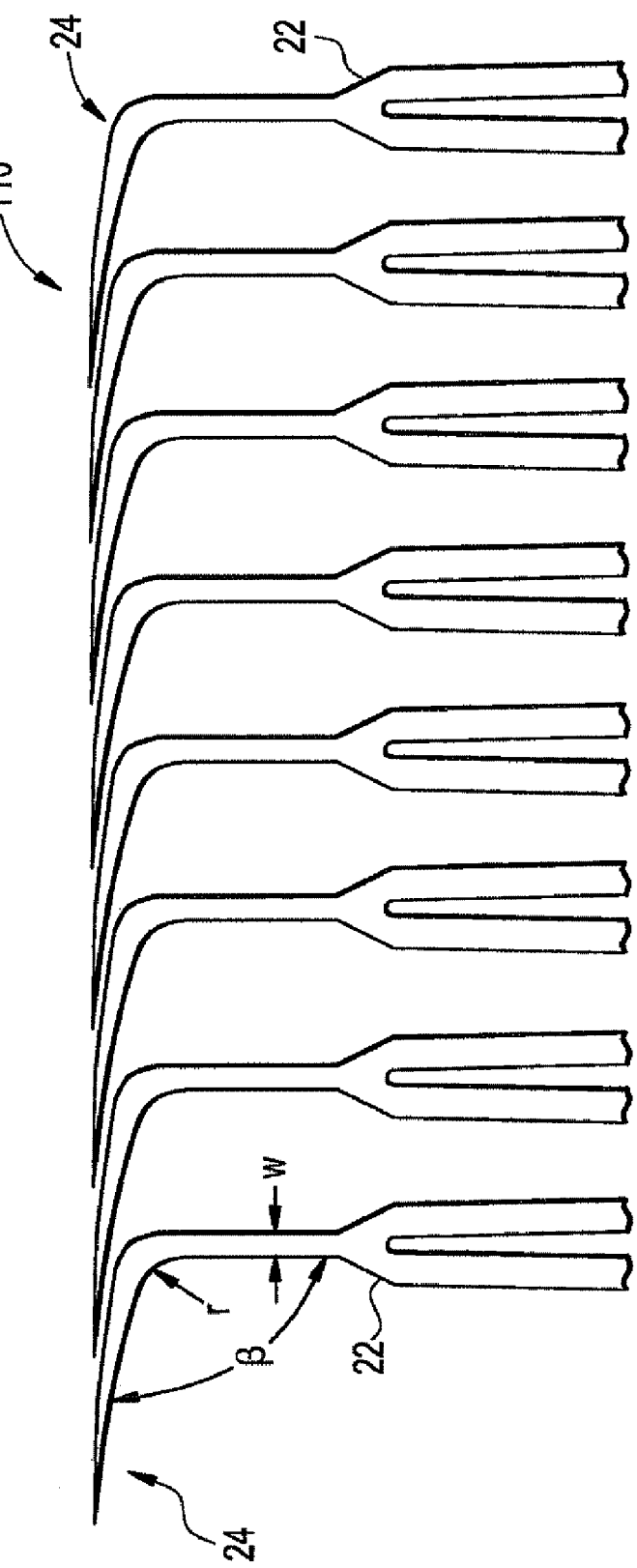

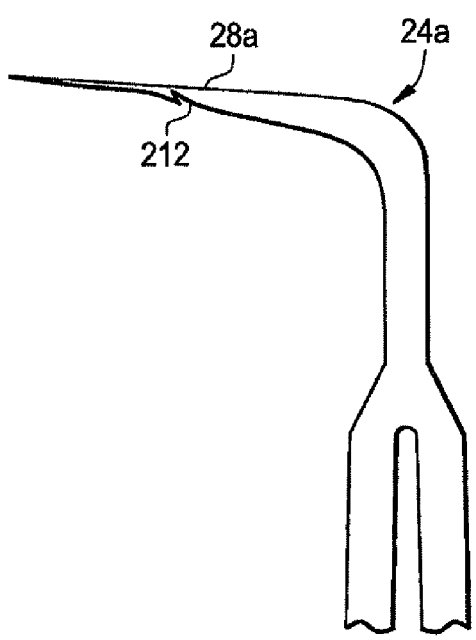 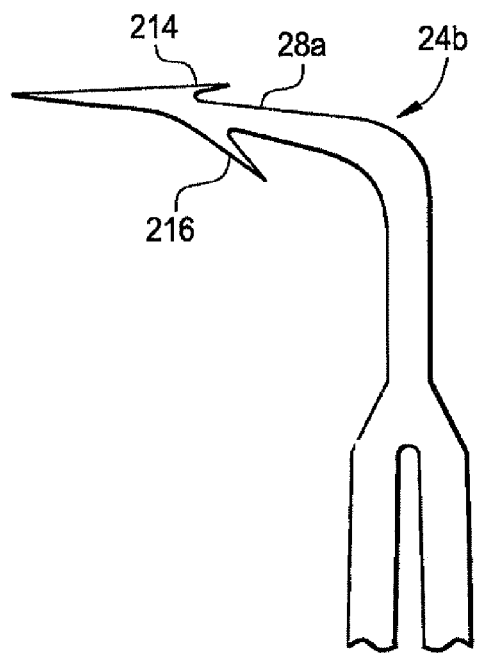

TWISTED ANCHORING BARB FOR STENT OF ABDOMINAL AORTIC ANEURYSM (AAA) DEVICE

CROSS-REFERENCE TO RELATED APPLICATION

This application is a divisional of U.S. application Ser. No. 11/488,198 filed Jul. 18, 2006, now U.S. Pat. No. 8,298,281.

BACKGROUND OF THE INVENTION

1. Field of the Invention

This invention relates broadly to surgical implants. More particularly, this invention relates to an anchoring portion of a stent particularly useful in synthetic grafts, although it is not limited thereto.

2. State of the Art

An aneurysm is an abnormal dilation of a layer or layers of an arterial wall, usually caused by a systemic collagen or structural defect. An abdominal aortic aneurysm (AAA) is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via a transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3 F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be highly durable, extendable and re-configurable while maintaining acute and long-term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta. In addition, the endoprostheses should preferably be percutaneously delivered and deployed such that surgical cut down is unnecessary.

A typical percutaneously delivered endoprosthesis for treating an abdominal aortic aneurism is a bifurcated device having a main body and two legs. Ideally, the device lines the aorta and extends from just below the lowest renal artery into both iliac arteries up to the juncture with the hypogastric arteries. It is generally comprised of a fabric material with an outer metallic stent structure. The stent supports the graft and holds it open within the vessels.

The endoprosthesis is delivered to the aneurysm in the aorta by way of a delivery catheter. The delivery catheter containing the endoprosthesis is inserted through a small incision in the groin where it is threaded through the femoral artery and advanced to the location of the aneurysm. The surgeon uses fluoroscopy to guide the endoprosthesis and the endoprosthesis has several markers to help the surgeon visualize the graft during placement of the endoprosthesis. It is desirable that there be at least 10 mm of overlap between the endoprosthesis and a healthy vessel portion. Otherwise, an opening between the two can develop that can lead to leakage. Generally, visualization and surgical technique is good enough to permit the end of the endoprosthesis to be placed within two millimeters of the intended target site to ensure the desired overlap.

Once the endoprosthesis is secured within the abdominal aorta, blood flow can continue through the aorta, passing through the endoprosthesis without filling the aneurysm. This is intended to prevent further ballooning and possible rupture of the aneurysm.

The vis attached to the wall of the aorta by the outward pressure of the stent against the aortic wall and by barbs which extend outward from the stent and penetrate into the aortic wall. Referring to Prior Art FIG. 1, several axes can be defined with respect to a barb of a stent: an X-axis extending tangential to the circumference of the stent, a Y-axis extending radially outward from the circumference of the stent, and a Z-axis extending parallel to a central longitudinal axis of the stent and through the stent wall. In the prior art, a barb 910 of the stent 912 is generally a longitudinally bent portion at the end of the stent which is coupled at 914 so as to spring outward relative to the longitudinal axis of the stent by sweeping an angle about the X-axis. The strength of the barb is dependent on the geometry of the coupling point 914. However, such coupling point 914 stiffness is compromised to permit the barb 910 to spring open to the desired angle once the end of the stent is released from the delivery catheter due to strain limitations. Referring to Prior Art FIG. 2, this weakness allows the barb to be deformed from a naturally open angle of $\alpha_1$ (e.g., approximately)45° to a more perpendicular orientation of angle $\alpha_1+\alpha_2$ (e.g., approximately)90° when the stent is subject to the forces F of blood flow. Thus, the manner in which the barb opens compromises the strength of the barb. Furthermore, the deformed configuration of such barbs may create stress risers and relatively high strain in the barb structure which results in barb fatigue.

In addition, referring to Prior Art FIG. 2, the angle $\alpha_1$ at which the barb 910 naturally initially opens to engage tissue is typically acute. Thus, to fully engage the aortic tissue with no further movement, the tissue of the aortic wall must move along the barb until seated against the outer surface of the stent. Such relative movement between the tissue and barb can cause the endoprosthesis to migrate relative to the aortic wall. Even migration of a few millimeters may result in undesirable leakage if there is less than desirable endoprosthesis/vessel overlap.

SUMMARY OF THE INVENTION

It is therefore an object of the invention to provide an anchoring barb structure for a stent.

It is also an object of the invention to provide a barb structure for a stent that decouples the barb open force from the strength of the barb.

It is another object of the invention to provide an endoprosthesis that will not migrate once placed within the target vessel.

It is a further object of the invention to provide a barb for a stent that has improved fatigue resistance.

It is also an object of the invention to provide a stent having an anchoring barb structure that can be compressed to a very small profile.

It is yet another object of the invention to provide a stent for that will not damage its delivery sheath.

It is yet another object of the invention to provide stent that meets the above objects and which is integrated into a stent graft, and particularly an abdominal aortic aneurysm stent graft.

In accord with these objects, which will be discussed in detail below, an endoprosthesis, particularly adapted as an abdominal aortic aneurysm (AAA) device, is bifurcated including a main body portion and two leg portions coupled thereto. Each portion includes a graft and a self-expanding stent formed from a superelastic material coupled relative to the graft. At one end of the main body portion, the apexes of the stent are provided with barbs. Each barb is twisted and shaped set to point radially outward. Preferably, each barb, as formed, also points substantially perpendicular to the longitudinal axis of the stent, even when in a non-deployed configuration. Thus, the motion to move the barb from a non-deployed configuration (within a delivery catheter) into a deployed configuration (for gripping tissue) is a twisting motion which moves the barb from being substantially aligned with the circumference of the stent to extending radially outwards from the stent.

Additional objects and advantages of the invention will become apparent to those skilled in the art upon reference to the detailed description taken in conjunction with the provided figures.

BRIEF DESCRIPTION OF THE DRAWINGS

Prior Art

FIG. 3 is a side elevation of an AAA device according to the invention, shown in an expanded state;

FIG. 4 is a perspective view of a barb according to the invention;

FIG. 9 is a diagram showing the reaction of the barb of the invention under deformational loading;

FIG. 10 is a laser pattern for cutting barbs on the stent according to the invention; and FIGS. 11 and 12 are laser pattern for cutting alternate embodiments of barbs according to the invention.

DETAILED DESCRIPTION OF THE PREFERRED EMBODIMENTS

Figure 4A:
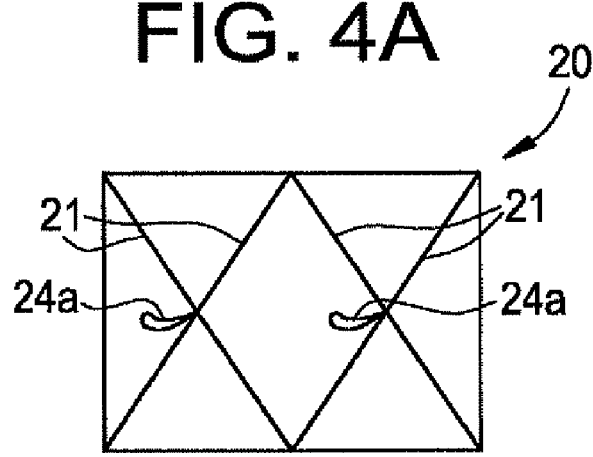
FIG. 4A is a broken side elevation of an alternative embodiment of an AAA device according to the invention, shown in an expanded state.
Figure 5:
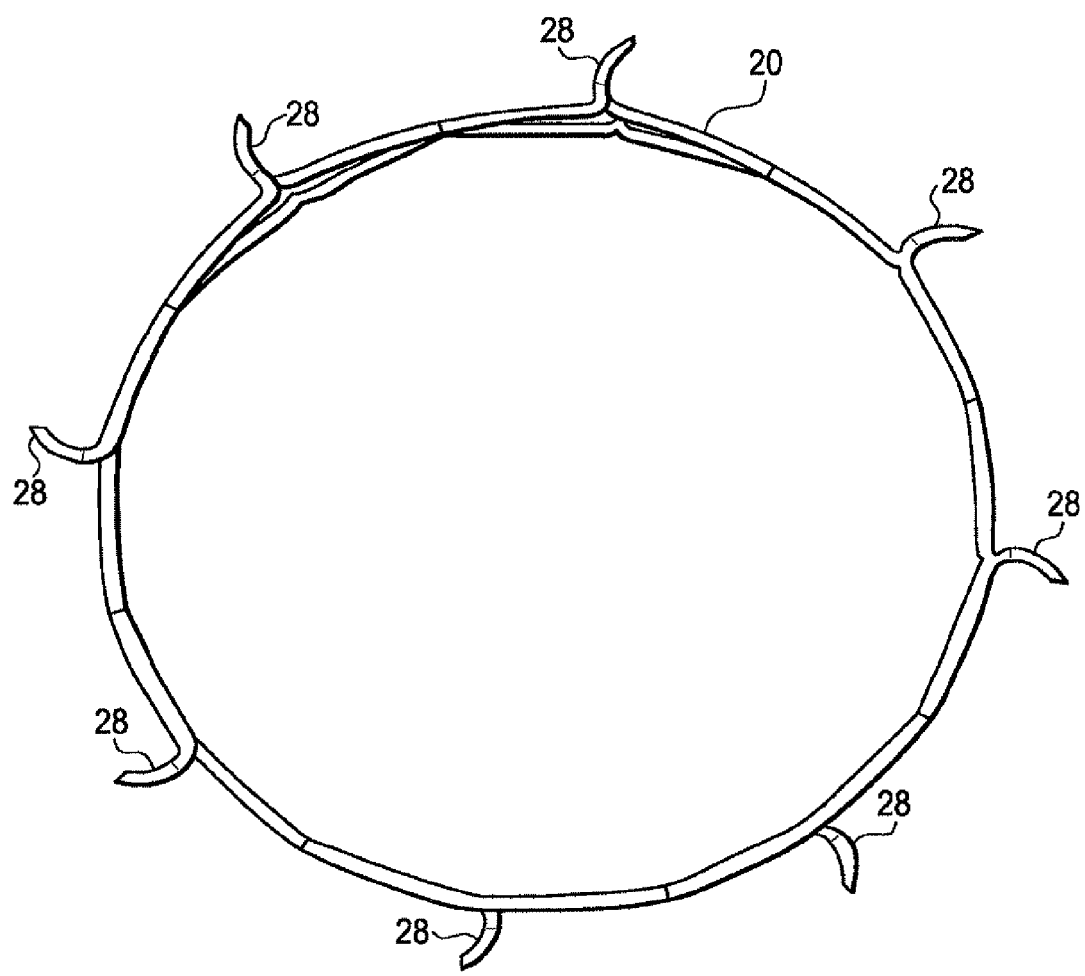
FIG. 5 is a end view of the AAA device according to the invention, shown in an expanded state.

Turning now to FIGS. 3 through 5, a vascular endoprosthesis 10 suitable for treatment of an abdominal aortic aneurysm (AAA) includes a main body portion 12 and two smaller leg portions 14, 16 coupled thereto in a generally inverted Y-configuration. Each portion includes a preferably artificial graft 18 and a self-expanding stent 20 coupled relative to the graft. The stent 20 is preferably formed from a superelastic, shape memory material such as Nitinol or other nickel-titanium alloy. At an upper end of the main body portion 12, the struts 21 of the stent 20 define apexes 22 that are provided with barbs 24 for coupling the main body portion to the abdominal aortic wall. Referring to FIG. 4A, the barbs 24a may alternatively or additionally be provided between the struts 21 at one or more intermediate locations along the length of the stent 20 between its ends.

Referring to FIGS. 4 and 5, each barb 24 includes a twisted neck 26 shape set via shape memory effect metallurgy principals. Several axes can be defined relative to each barb 24: an X-axis extending tangential to the circumference of the stent, a Y-axis extending radially outward from the circumference of the stent, and a Z-axis extending through the neck 26 of the barb 24. The shape set biases the neck 26 to rotate about the Z-axis and point an anchor portion 28 of the barb radially outward relative to the longitudinal axis $A_L$ of the stent 20 of the main body portion 12 such that the barb extends in alignment with the Y-axis. In a preferred embodiment, each anchor portion 28, as formed, is also oriented substantially perpendicular (e.g., 90°±15° relative to the Z-axis, even when in the non-deployed configurations of FIGS. 6 and 7.

Figure 6:
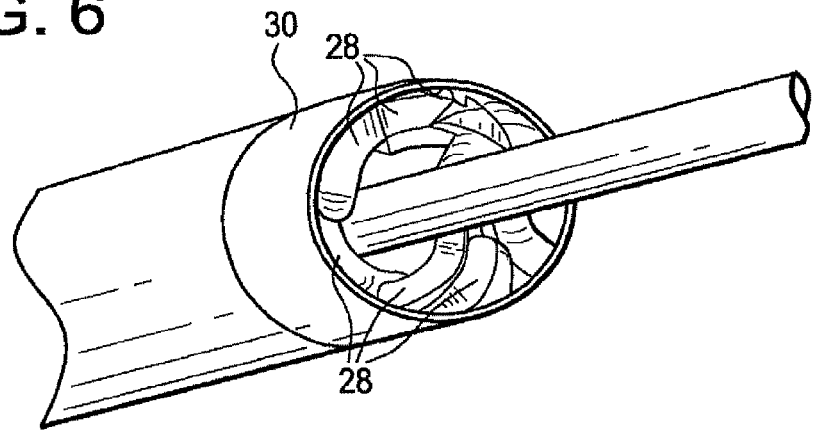
FIG. 6 is a perspective view of the AAA of the invention shown completely within a delivery catheter.
Figure 7:
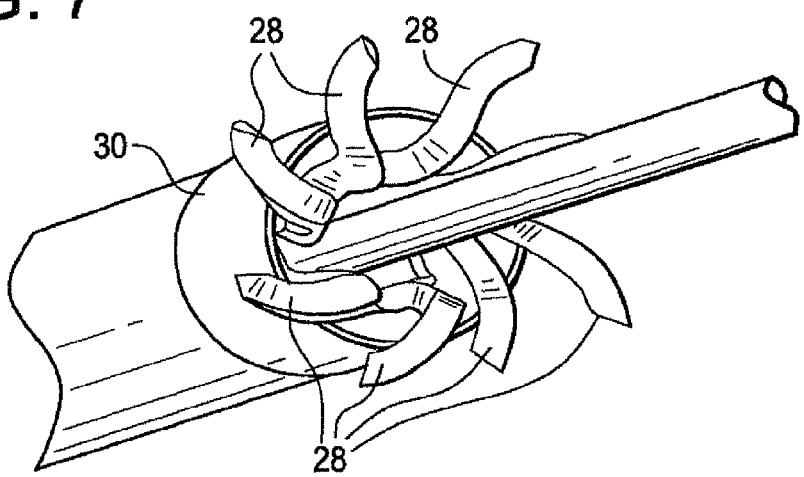
FIGS. 7 and 8 are perspective views of the AAA of the invention shown partially deployed from a delivery catheter.
Figure 8:
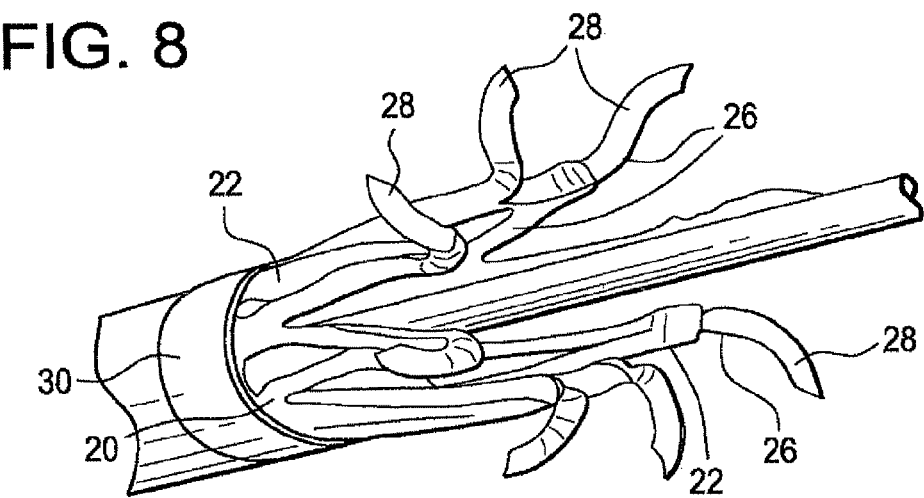

Referring to FIGS. 6 through 8, the motion to move each barb 22 into a deployed configuration for gripping the abdominal aortic wall is a twisting motion about the Z-axis which twists each barb 22 about its neck 24 into its stress free shape. Such motion moves the anchor portion 28 of each barb 22 from being substantially aligned with the circumference of the stent 20 when the stent is in a compressed non-deployed state within the delivery catheter 30 (FIG. 6) to extending radially outwards from the stent when in an expanded deployed state (from FIGS. 7 to 8, and eventually to the configuration shown back in FIG. 5). This motion causes the anchor to penetrate the tissue substantially perpendicularly, eliminating any acute tissue migration. It is appreciated that the exact angle of penetration can be designed to optimize migration resistance and downward movement of the endoprosthesis 10 under load of blood flow through the graft 18.

Figure 1:
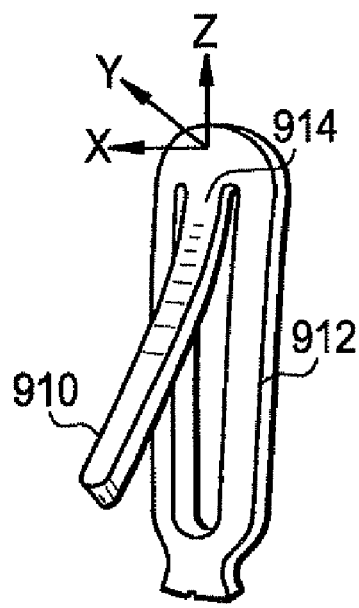
FIG. 1 is a perspective view of a exemplar conventional barb for a stent in an AAA device; and Prior Art
Figure 2:
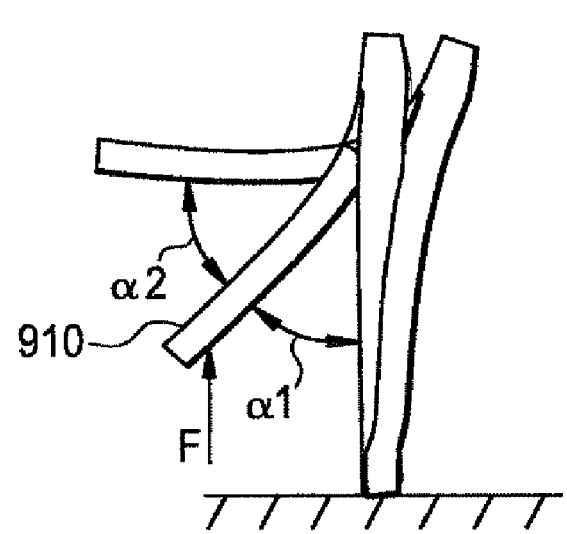
FIG. 2 shows the reaction of the Prior Art barb of FIG. 1 under deformational loading.

An important aspect of the invention is that the opening motion of the barb (deployed by the shaped set twist) is decoupled from the strength of the barb, thereby allowing a much stronger barb. Finite element analysis models indicate that designs according to the invention are substantially stronger than conventional designs. In addition, referring to FIG. 9, under a bending load of suitable force F to cause migration if the barb were not sufficiently strong, the stress and strain are distributed over a wider area and have much lower values than in conventional designs and the barb deflects a smaller angular displacement $\alpha_3$ relative to conventional designs (as seen by comparing $\alpha_3$ relative to $\alpha_2$ in Prior Art FIG. 2). While conventional designs have inherent weaknesses to allow the barb to open, it is possible to stiffen and strengthen the barb in the present design, as discussed below, to minimize $\alpha_3$ (to approach zero) without any loss of opening function. Thus, the present design has a relatively an increased resistance to fatigue.

Beam theory provides that the strength of a beam is primarily affected by its thickness rather than its width. Because the neck 26 of the barb 24 is twisted, the width of the neck becomes its thickness in the radial direction, which provides great advantage for design flexibility. For a given wall thickness of starting stent tubing, by changing the width to which the barbs are cut, the stiffness of the barbs are easily changed.

FIG. 10 shows a laser cut pattern 110 for cutting a series of apexes and barbs on a shape memory alloy tube (or flat which can be bent into a tube) for creating the stent 20 for use in the endoprosthesis according to the invention. The barb angle β can be modified to optimize the anchoring force and the stress/strain distribution. The radius r of the barb can be modified to accommodate more barbs and to change the stiffness of the barbs. As discussed above, the width w of the barbs can be modified to change the stiffness of the barbs and to lower the strain during forming. By way of one example, and not by limitation, the barb angle β can be 103°, the radius r can be 0.0150 inch and the width w can be 0.0100 inch.

The anchors of the barbs may include reverse barbs which increase pullout force. FIG. 11 shows as laser cut pattern for a reverse barb 212 that is recessed relative to the anchor 28a of the barb 24a, while FIG. 12 shows laser cut pattern for reverse barbs 214, 216 that extend outward from the anchor 28a of barb 24b.

There have been described and illustrated herein embodiments of barb design for a stent. While particular embodiments of the invention have been described with reference to an endoluminal prosthesis, particularly suitable for an AAA device, it is not intended that the invention be limited thereto, as it is intended that the invention be as broad in scope as the art will allow and that the specification be read likewise. Thus, the barb design of the invention may be used on stents intended for other purposes. In addition, shape memory alloys, and preferably Nitinol have been disclosed as preferred materials for use in practicing the invention, it will be understood that other shape memory alloys and other shape set materials including biocompatible plastics may be used as well. It will therefore be appreciated by those skilled in the art that yet other modifications could be made to the provided invention without deviating from its spirit and scope as claimed.

What is claimed is:

1. A stent, comprising:
a metallic tubular member cut into features having widths, lengths and thicknesses, including struts and defining a circumference, a longitudinal axis and a radial axis; and
a barb, the barb including an anchor portion and a shape set twisted neck, the shape set twisted neck being biased and configured to twist along its length, rotating the barb radially outward relative to the longitudinal axis of the tubular member, the barb being a part and extending from an intersection of struts forming the stent, the shape set twisted neck cut from the tubular member with a predetermined width and twisted about 90 degrees such that its width becomes its thickness, thereby increasing its strength, the tubular member and the barb being a one-piece, unitary structure, said stent and barb together defining three axes, an X-axis extending tangential to a circumference of said stent, a Y-axis extending radially outward from the circumference of said stent, and a Z-axis extending through said neck portion of said barb, and said neck portion is shape set biased to twist along said Z-axis.

2. The stent according to claim 1, wherein:
said stent and barb together defining three axes, an X-axis extending tangential to a circumference of said stent, a Y-axis extending radially outward from the circumference of said stent, and a Z-axis extending through said neck portion of said barb,
wherein said neck portion is shape set biased to rotate said anchor portion about said Z-axis.

3. The stent according to claim 2, wherein:
said anchor portion, as formed, is oriented substantially perpendicular relative to said Z-axis.

4. The stent according to claim 1, wherein:
said stent is movable between a collapsed non-deployed configuration and an expanded deployed configuration, and when said stent is in said non-deployed configuration said anchor portion is substantially oriented about said circumference of said stent.

5. The stent according to claim 2, wherein:
when said stent is in said deployed configuration, said anchor portion is oriented substantially radially relative to said Z-axis.

6. The stent according to claim 1, wherein:
said neck portion rotates said anchor portion of said barb into orientation during expansion into said deployed configuration.

7. The stent according to claim 1, wherein:
said stent is a self-expanding stent.

* * * * *